United States Patent
Omura et al.

(10) Patent No.: US 8,697,750 B2
(45) Date of Patent: Apr. 15, 2014

(54) OIL-IN-WATER TYPE EMULSION SKIN COSMETIC

(75) Inventors: Takayuki Omura, Yokohama (JP); Tomomi Furukawara, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/701,942

(22) PCT Filed: Jun. 6, 2011

(86) PCT No.: PCT/JP2011/062892
§ 371 (c)(1),
(2), (4) Date: Dec. 4, 2012

(87) PCT Pub. No.: WO2011/158678
PCT Pub. Date: Dec. 22, 2011

(65) Prior Publication Data
US 2013/0079410 A1    Mar. 28, 2013

(30) Foreign Application Priority Data

Jun. 17, 2010  (JP) ................................ 2010-138388
Jun. 3, 2011   (JP) ................................ 2011-125099

(51) Int. Cl.
*A61K 8/44*   (2006.01)
*A61K 9/00*   (2006.01)

(52) U.S. Cl.
USPC ......................................... 514/561; 424/400

(58) Field of Classification Search
USPC ......................................... 514/561; 424/400
See application file for complete search history.

(56) References Cited

U.S. PATENT DOCUMENTS

| | | | | |
|---|---|---|---|---|
| 4,482,537 A | * | 11/1984 | El-Menshawy et al. | ......... 424/59 |
| 5,061,721 A | * | 10/1991 | Cordi et al. | ................... 514/376 |
| 2008/0200362 A1 | * | 8/2008 | Cho et al. | ...................... 510/446 |
| 2010/0292509 A1 | * | 11/2010 | Kajiya et al. | .................. 564/164 |

FOREIGN PATENT DOCUMENTS

| | | |
|---|---|---|
| JP | 11-60436 | 3/1999 |
| JP | 2006-327971 | 12/2006 |
| JP | 2008-1654 | 1/2008 |
| JP | 2009-221121 | 10/2009 |
| JP | 2009-298752 | 12/2009 |
| WO | WO 2009/093534 | 7/2009 |
| WO | WO 2010/064678 | 6/2010 |

OTHER PUBLICATIONS

International Serach Report for PCT/JP2011/062892, dated Aug. 16, 2011, English 2 pgs and JP 3 pgs.

* cited by examiner

*Primary Examiner* — Blessing M Fubara
*Assistant Examiner* — Jennifer A Berrios
(74) *Attorney, Agent, or Firm* — Andrew F. Young, Esq.; Lackenbach Siegel, LLP

(57) ABSTRACT

An oil-in-water type emulsion skin cosmetic which can be spread on skin easily. The formulation can contain glycerin at a high concentration or a formulation containing a combination of glycerin and an acrylamide-type thickening agent without the sticky effect. The skin cosmetic is characterized by comprising (A) a D-amino acid or a derivative or salt thereof, (B) a homopolymer, a copolymer or a crosspolymer containing at least one component selected from 2-acrylamide-2-methylpropanesulfonic acid. acrylic acid and derivatives thereof as a constituent unit, (C) an ester oil with an IOB value of 0.2 to 0.6, and (D) glycerin.

4 Claims, No Drawings

OIL-IN-WATER TYPE EMULSION SKIN COSMETIC

CROSS REFERENCE TO RELATED APPLICATIONS

This application claims priority to International Ser. No. PCT/JP2011/062892 filed Jun. 6. 2011, the entire contents of which are incorporated herein fully by reference, which in turn claims priority to JP Ser. No. JP 2010-138388, filed on Jun. 17, 2010 and JP 2011-125099 filed on Jun. 3, 2011.

TECHNICAL FIELD

The invention relates to an oil-in-water type emulsion skin cosmetic composition having good texture and stability. More specifically, the invention relates to an oil-in-water type emulsion skin cosmetic composition having light spreadability on skin, no stickiness, lightness, a good feeling as an active ingredient effectively penetrates into the skin (good penetrating feeling), and high stability over time.

BACKGROUND ART

Glycerin is known as a cosmetic ingredient having a high moisturizing effect and a high skin improving effect such as a high skin roughness reducing effect. To produce such a high skin improving effect significantly, glycerin is often added at a content of 5.0% by mass or more. Particularly, skin cosmetics with high glycerin content can produce high skin improving effect but may have the disadvantage in use that as the content increases, dewy feeling or feeling as an active ingredient penetrates into the skin disappears, and stickiness appears.

In recent years, there have been attempts, such as the addition of fatty acid glycerin ester, the addition of specific water-soluble solid silicone, and the addition of organosiloxane elastomer spherical particles, to reduce stickiness caused by the addition of glycerin and to obtain a light feeling (see Patent Documents 1 to 3).

However, these conventional techniques tend to reduce the skin improving effect of glycerin in conflict with a certain stickiness reducing effect produced by the addition of the above additive.

On the other hand, acrylamide thickeners, which are used as cosmetic thickeners, provide good texture such as good compatibility to the skin or good spreadability (see for example Patent Documents 4 and 5). Such acrylamide thickeners are useful as an alternative to carboxyvinyl polymer, xanthan gum, or hydroxyethyl cellulose, which is traditionally used as a cosmetic thickener in many cases. However, when glycerin is added at a high concentration to provide a skin improving effect, a problem also occurs in which good texture of acrylamide thickeners is lost and it becomes impossible to reduce the glycerin-induced stickiness.

PRIOR ART PUBLICATIONS

Patent Documents

Patent Document 1: JP-A Hei 11-246329
Patent Document 2: JP-A 2000-191428
Patent Document 3: JP-A 2002-356416
Patent Document 4: JP-A Hei 10-67685
Patent Document 5: JP-A 2001-114641

SUMMARY OF INVENTION

Problems to be Solved by the Invention

It is therefore an object of the invention to solve the conventional problems and to provide an oil-in-water type emulsion skin cosmetic composition that has light spreadability on skin, no stickiness, and a good penetrating feeling as an active ingredient effectively penetrates into the skin, provides moisture, and is moist even in a system with a high glycerin content or in a system used in combination with an acrylamide thickener, and also allows glycerin to produce a high skin improving effect.

Means for Solving the Problems

As a result of earnest studies to solve the problems, the present inventors have accomplished the invention based on the finding that even in a system with a high glycerin content, an oil-in-water type emulsion skin cosmetic composition containing (A) a D-amino acid or a derivative or salt thereof, (B) a homopolymer, a copolymer, or a crosspolymer including, as a constituent unit, one or more selected from 2-acrylamido-2-methylpropanesulfonic acid, acrylic acid, and derivatives thereof, (C) an ester oil with an IOB value of 0.2 to 0.6, and (D) glycerin is compatible to the skin and not sticky during use, and can reliably produce a skin improving effect.

Effects of the Invention

According to the invention, there is provided an oil-in-water type emulsion skin cosmetic composition that has light spreadability on skin, no stickiness, and a good penetrating feeling when an active ingredient penetrates the skin, provides moisture, and is moist even in a system with a high glycerin content, and also allows glycerin to produce a high skin improving effect.

MODES FOR CARRYING OUT THE INVENTION

Hereinafter, the invention is described in detail.

The skin cosmetic composition of the invention essentially contains a D-amino acid or a derivative or salt thereof (ingredient (A), hereinafter also abbreviated as "D-amino acid material"). As used herein, the term "D-amino acid or a derivative or salt thereof (D-amino acid material)" means a D-amino acid, a derivative thereof, a salt thereof, or a mixture thereof.

It is well known that amino acids can exist in L-form or D-form which are optical isomers and natural proteins are composed of L-amino acids bonded together by peptide bonds. It has been considered that except for some cases such as bacterial cell walls, only L-amino acids exist in mammals including human and only L-amino acids are used in living bodies. Conventionally, therefore, academic or industrial focus and research have been dominantly on L-amino acids.

Exceptional cases where D-amino acids are used include (1) cases where D-amino acids are used as raw materials for antibiotics to be produced by bacteria and (2) cases where food additives contain a mixture of L- and D-amino acids in order to avoid the cost required to isolate the L-amino acid from the mixture (racemic mixture) containing equal amounts of the L- and D-amino acids synthesized chemically.

Recently, it has been found that even in the human body, D-aspartic acid (D-Asp), which does not occur naturally, increases with age in the ocular lens, brain, or skin, and the relationship between it and the development of cataract or Alzheimer's disease has begun to be discussed (Tadatoshi Kinouchi et al. "Proteins, Nucleic Acids, and Enzymes" (in Japanese) Vol. 50, No. 5 (2005), 453-560). Also in the skin, accumulation of D-Asp has been found to be caused by aging or ultraviolet irradiation, and it has been proposed that D-Asp be used as a molecular marker for detecting skin damage caused by aging or ultraviolet rays (Noriko Fujii, Annual Report of Cosmetology (in Japanese), No. 13 (2005). However, no examples are known in which D-amino acids are positively used as biologically active materials.

Under the above circumstances, the invention is characterized in that a D-amino acid, which has not been conventionally added to cosmetics, especially skin cosmetics, is added as an essential ingredient.

The D-amino acid material (ingredient (A)) used in the invention may be of any type as long as it is in the D-form. Preferably, the D-amino acid material itself can be effective in improving the skin. Examples include D-aspartic acid, which can have an antioxidant effect and a collagen production promoting effect, D-alanine, which can have a laminin 332 production promoting effect and a collagen production promoting effect, D-glutamic acid, which can have a barrier recovery function, a wrinkle formation reducing effect, and a skin roughness reducing effect, D-serine, which can have an ultraviolet damage reducing effect, D-hydroxyproline, which can have a laminin 332 production promoting effect, D-cysteine, which can have an ultraviolet damage reducing effect, D-methionine and D-proline, which can have an ultraviolet damage reducing effect, and D-hydroxyproline, which can have a melanin production inhibiting effect.

The D-amino acid material used in the invention may be a synthetic product or a commercially available product.

For example, a known method for producing a D-amino acid includes allowing bacterial D-aminoacylase to act on an acylated amino acid to obtain a D-amino acid (see JP-A Hei 11-113592).

The content of the D-amino acid material in the skin cosmetic composition of the invention is preferably from 0.1 to 5.0% by mass based on the total amount of the cosmetic composition.

Next, a detailed description is given of a homopolymer, a copolymer, or a crosspolymer including, as a constituent unit, one or more selected from 2-acrylamido-2-methylpropanesulfonic acid (hereinafter also abbreviated as "AMPS"), acrylic acid, and derivatives thereof, which is used as the ingredient (B) in the invention.

Examples of the ingredient (B) used in the invention include a vinylpyrrolidone/2-acrylamido-2-methylpropanesulfonic acid (salt) copolymer, a dimethylacrylamide/2-acrylamido-2-methylpropanesulfonic acid (salt) copolymer, an acrylamide/2-acrylamido-2-methylpropanesulfonic acid copolymer, a methylenebisacrylamide-crosslinked dimethylacrylamide/2-acrylamido-2-methylpropanesulfonic acid crosspolymer, a mixture of polyacrylamide and poly(sodium acrylate), a sodium acrylate/2-acrylamido-2-methylpropanesulfonic acid copolymer, a hydroxyethyl acrylate/2-acrylamido-2-methylpropanesulfonic acid (salt) copolymer, poly(ammonium acrylate), a polyacrylamide/ammonium acrylate copolymer, and an acrylamide/sodium acrylate copolymer. Further examples include acrylamide/acrylic acid/2-acrylamido-2-methylpropanesulfonic acid (salt) copolymer, homopolymer of 2-acrylamido-2-methylpropanesulfonic acid (salt), and vinylformamide/2-acrylamido-2-methylpropanesulfonic acid (salt)copolymer. It will be understood that these are non-limiting examples.

In the above polymers, preferred examples of the salt include an alkali metal salt (such as a calcium salt or a magnesium salt), an ammonium salt, and an organic amine salt (such as a monoethanolamine salt, a diethanolamine salt, or a triethanolamine salt). One or more of these (B) ingredients may be used.

These (B) ingredients may be synthetic products or commercially available products. Examples include ARISTOFLEX AVC (manufactured by Clariant), which corresponds to a vinylpyrrolidone/2-acrylamido-2-methylpropanesulfonic acid (salt) copolymer, SIMULGEL EG (manufactured by SEPIC) and SIMULGEL EPG (manufactured by SEPIC), which each correspond to a sodium acrylate/2-acrylamido-2-methylpropanesulfonic acid (salt) copolymer, SIMULGEL 600 (manufactured by SEPIC), which corresponds to an acrylamide/2-acrylamido-2-methylpropanesulfonic acid sodium salt copolymer, SEPIGEL 305 (manufactured by SEPIC) and SEPIGEL 501 (manufactured by SEPIC), which each correspond to an acrylamide/2-acrylamido-2-methylpropanesulfonic acid (salt) copolymer, Hostacerin AMPS (manufactured by Clariant) and SIMULGEL 800 (manufactured by SEPIC), which each correspond to a homopolymer of 2-acrylamido-2-methylpropanesulfonic acid sodium salt, and SU-POLYMER G-1 (manufactured by TOHO Chemical Industry Co., Ltd.), which corresponds to a dimethylacrylamide/2-acrylamido-2-methylpropanesulfonic acid copolymer.

The content of the ingredient (B) in the skin cosmetic composition of the invention is preferably from 0.1 to 2.0% by mass, more preferably from 0.3 to 1.5% by mass, based on the total amount of the cosmetic composition. If the content is less than 0.1% by mass, a phenomenon such separation, oil floating, demulsification, or aggregation can be more likely to occur, which is not preferred in view of stability. On the other hand, the ingredient (B) added at a content of more than 2.0% by mass will no longer increase the effects of the invention and may contrarily produce a sticky feeling.

Next, a detailed description is given of an ester oil with an IOB value of 0.2 to 0.6, the ingredient (C), used in the invention. IOB value is ordinarily used to describe a compound's "organic nature" in the organic chemistry. When considering the factors that affect various characteristics of an organic compound having hydrocarbons in its basic structure, it can be considered that the characteristics are based on two factors, i.e., the "organic nature" of hydrocarbons composed of the chain of covalent bonds of carbon chains and the "inorganic nature" from the influence of the electric affinity (ion) that exists in the substitution radicals (functional group). "Organic value" or "inorganic value" is determined as a sum of values from each organic and inorganic structural component of the compound. The ratio of an organic value and an inorganic value in the is provided by "inorganic value (IV)/organic value (OV)=IOB".

The ingredient (C) used in the invention may be any ester oil with an IOB value of 0.2 to 0.6. Examples include tripropylene glycol dineopentanoate (IOB=0.52) isodecyl benzoate (IOB=0.23), propylene glycol dicaprylate (IOB=0.32), isononyl isononanoate (IOB=0.2), cetyl 2-ethylhexanoate (IOB=0.52) glyceryl tri-2-ethylhexanoate (IOB=0.36) isodecyl neopentanoate IOB=0.22), 2-ethylhexyl 2-ethylhexanoate (IOB=0.2), pentaerythritol tetra-2-ethylhexanoate (IOB=0.35), di-2-ethylhexyl succinate (IOB=0.32), and 2-ethylhexyl isononanoate (IOB=0.2).

One or more of these ester oils may be used.

Particularly in view of texture, the content of the ingredient (C) in the skin cosmetic composition of the invention is preferably from 1.0 to 15.0% by mass, more preferably from 3.0 to 12.0% by mass, based on the total amount of the cosmetic composition. If the content is less than 1.0% by mass, an advantageous effect of the invention, specifically, suppression of stickiness and production of a penetrating feeling may be insufficient.

Next, a description is given of glycerin, the ingredient (D), used in the invention.

The ingredient (D) used in the invention may be glycerin commonly used in cosmetics, which may be a synthetic product or a commercially-available product.

In the invention, glycerin (the ingredient (D)), which is known to be highly effective in improving the skin but to be sticky, may be used at a content of as relatively high as 5.0 to 15.0% by mass based on the total amount of the cosmetic composition, so that the effect of improving the skin can be reliably obtained. On the other hand, the ingredients (A), (B), and (C) are mixed with it, so that a non-sticky cosmetic composition can be obtained.

The oil-in-water type emulsion skin cosmetic composition of the invention may be produced by adding a water-phase component to an oil-phase component and stirring and mixing them by a conventional method with a homogenizer or the like. The water-phase component may contain various water-soluble ingredients in water or in an aqueous phase composed mainly of water. The content of the water-phase component is preferably from 50.0 to 80.0% by mass based on the total amount of the oil-in-water emulsion skin cosmetic composition. If the water-phase component is less than 50.0% by mass, heavy feeling or stickiness may occur. On the other hand, if it is more than 80.0% by mass, the cosmetic composition will be light but not moist, so that a high skin improving effect, an advantageous effect of the invention, can be sometimes hard to obtain.

Besides the above essential ingredients, other ingredients that can be usually added to emulsion cosmetics may be appropriately added to the oil-in-water type emulsion cosmetic composition of the invention as long as the effects of the invention are not impaired.

Examples of such other ingredients include, but are not limited to, ultraviolet absorbers, ultraviolet scattering agents, waxes, hydrocarbon oils, fatty acid esters, silicone oils, polyhydric alcohols, water-soluble polymers, higher alcohols, higher fatty acids, and active agents.

Examples of ultraviolet absorbers include p-aminobenzoic acid, octyl-p-methoxycinnamate (2-ethylhexyl-p-methoxycinnamate), glyceryl mono-2-ethylhexanoyl-di-p-methoxycinnamate, methyl bis(trimethylsiloxane)silylisopentyl trimethoxycinnamate, and other cinnamic acid derivative ultraviolet absorbers, 2,2'-hydroxy-5-methylphenylbenzotriazole, 2-(2'-hydroxy-5'-t-octylphenyl)benzotriazole, 2-(2-hydroxy-5'-methylphenyl benzotriazole, 4-methoxy-4'-t-butyldibenzoylmethane, 5-(3,3-dimethyl-2-norbornylidene)-3-pentan-2-one, bis-ethylhexyloxyphenol-methoxyphenyl-triazine, 2,4,6-tris[4-(2-ethylhexyloxycarbonyl)anilino]1,3,5-triazine, dimorpholinopyridazinone, and 2-ethylhexyl-2-cyano-3,3-diphenylacrylate.

Examples of ultraviolet scattering agents include fine particles with an average particle size of 10 to 100 nm, such as fine particles of titanium oxide, fine particles of zinc oxide, fine particles of iron oxide, and fine particles of cerium oxide.

Ultraviolet scattering agents hydrophobized by a silicone treatment with methyl hydrogen polysiloxane or a silane coupling agent, by a metal soap treatment, by a fluorine treatment with a perfluoroalkylphosphoric acid diethanolamine salt or perfluoroalkylsilane, by a dextrin fatty acid ester treatment, or by other methods may also be added as needed depending on the dosage form.

Examples of waxes include beeswax, candelilla wax, carnauba wax, lanolin, liquid lanolin, and jojoba wax.

Examples of hydrocarbon oils include liquid paraffin, ozocerite, squalane, pristane, paraffin, ceresin, squalene, petrolatum, microcrystalline wax, polyethylene wax, and Fischer-Tropsch wax.

Examples of fatty acid esters include cetyl palmitate, cholesteryl stearate, and beeswax fatty acid 2-octyldodecyl ester.

Examples of silicone oils include chain polysiloxanes (e.g., dimethylpolysiloxane, methylphenylpolysiloxane, and diphenylpolysiloxane); cyclic polysiloxanes (e.g., decamethylcyclopentasiloxane and dodecamethylcyclohexasiloxane), silicone resins forming a three-dimensional network structure, silicone rubbers with an average molecular weight of 200,000 or more, and various modified polysiloxanes (such as amino-modified polysiloxanes, polyether-modified polysiloxanes, alkyl-modified polysiloxanes, and fluorine-modified polysiloxanes).

Examples of polyhydric alcohols include polyethylene glycol, glycerin, diglycerin, 1,3-butylene glycol, erythritol, sorbitol, xylitol, maltitol, 1,2-pentanediol, and hexylene glycol.

Examples of water-soluble polymers include carrageenan, pectin, mannan, curdlan, chondroitin sulfate, starch, glycogen, gum arabic, sodium hyaluronate, tragacanth gum, xanthan gum, mucoitin sulfuric acid, hydroxyethyl guar gum, carboxymethyl guar gum, guar gum, dextran, keratosulfate, locust bean gum, succinoglucan, chitin, chitosan, carboxymethyl chitin, and agar.

Examples of higher alcohols include hexyl alcohol, octyl alcohol, cetyl alcohol, stearyl alcohol, ceryl alcohol, behenyl alcohol, triacontyl alcohol, cerakyl alcohol, and batyl alcohol.

Examples of higher fatty acids include lauric acid, myristic acid, palmitic acid, stearic acid, and behenic acid.

Example of active agents include salts of L-ascorbic acid and derivatives thereof, salts of tranexamic acid and derivatives thereof, salts of alkoxysalicylic acid and derivatives thereof, and salts of glutathione and derivatives thereof. More specifically, L-ascorbic acid derivatives include L-ascorbic acid monoalkyl esters such as L-ascorbic acid monostearate, L-ascorbic acid monopalmitate, and L-ascorbic acid monooleate; L-ascorbic acid monoesters such as L-ascorbic acid monophosphate and L-ascorbic acid-2-sulfate; L-ascorbic acid dialkyl esters such as L-ascorbic acid distearate, L-ascorbic acid dipalmitate, and L-ascorbic acid dioleate; L-ascorbic acid trialkyl esters such as L-ascorbic acid tristearate, L-ascorbic acid tripalmitate, and L-ascorbic acid trioleate; L-ascorbic acid triesters such as L-ascorbic acid triphosphate; and L-ascorbic acid glucosides such as L-ascorbic acid 2-glucoside. In the invention, L-ascorbic acid, L-ascorbic acid phosphate, L-ascorbic acid-2-sulfate, and L-ascorbic acid 2-glucoside are each preferably used in the form of a salt.

Examples of tranexamic acid derivatives include tranexamic acid dimers (e.g., trans-4-(trans-aminomethylcyclohexanecarbonyl)aminomethylcyclohexanecarboxylic acid hydrochloride), tranexamic acid hydroquinone esters (e.g., 4-(trans-aminomethylcyclohexanecarboxylic acid 4'-hydroxyphenyl ester), tranexamic acid gentisic acid esters (e.g., 2-(trans-4-aminomethylcyclohexylcarbonyloxy)-5-hydroxybenzoic acid), and tranexamic acid amides (e.g., trans-4-aminomethylcyclohexanecarboxylic acid methylamide, trans-4-(p-methoxybenzoyl)aminomethylcyclohexanecarboxylic acid, and trans-4-guanidinomethylcyclohexanecarboxylic acid). In the invention, tranexamic acid or a tranexamic acid derivative is preferably used in the form of a salt.

Alkoxysalicylic acid is a salicylic acid derivative in which the hydrogen atom at 3, 4, or 5 position of salicylic acid is replaced by an alkoxy group. The alkoxy group as a substituent is preferably any one of methoxy, ethoxy, propoxy, isopropoxy, butoxy, and isobutoxy groups, more preferably a methoxy group or an ethoxy group. Examples of such a compound include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, and 5-propoxysalicylic acid. In the invention, alkoxysalicylic acid and a derivative thereof (such as an ester) are each preferably used in the form of a salt.

Examples of the salts of drugs include, but are not limited to, alkali metal or alkaline-earth metal salts such as sodium salts, potassium salts, and calcium salts, and other salts such as ammonium salts and amino acid salts.

Other ingredients that may be added also include vitamin A, vitamin A derivatives such as vitamin A palmitate and vitamin A acetate, vitamin B6 hydrochloride, vitamin $B_6$ tripalmitate, vitamin $B_6$ dioctanoate, vitamin $B_2$ and derivatives thereof, vitamin $B_{12}$, vitamin $B_{15}$ and derivatives thereof, and other vitamin B materials, α-tocopherol, β-tocopherol, vitamin E acetate, and other vitamin E materials, vitamin D materials, vitamin H, pantothenic acid, pantethine, and other vitamins; γ-oryzanol, allantoin, glycyrrhizinic acid (salt), glycyrrhetinic acid, stearyl glycyrrhetinate, hinokitiol, bisabolol, eukalypton, thymol, inositol, saikosaponin, carrot saponin, sponge gourd saponin, mukurossi peel saponin, and other saponins, pantothenyl ethyl ether, arbutin, cepharanthine, and other various medicines, extracts of plants such as curly dock, sophora, Nuphar, orange, sage, yarrow, mallow, swertia herb, thyme, Japanese angelica root, spruce, white birch, horsetail, sponge gourd, horse chestnut, saxifrage, scutellaria root, arnica, lily, mugwort, peony, aloe, gardenia, and cherry leaf, and β-carotene and other colorants.

Other ingredients also include lower alcohols such as ethanol; antioxidants such as butylhydroxytoluene, δ-tocopherol, and phytin; preservatives such as benzoic acid, salicylic acid, sorbic acid, alkyl p-oxybenzoate, phenoxyethanol, hexachlorophene, and ε-polylysine; and organic or inorganic acids such as citric acid, lactic acid, and hexametaphosphoric acid, and salts thereof.

Examples of the form of the oil-in-water type emulsion skin cosmetic composition of the invention include, but are not limited to, skin milk, skin cream, hair cream, liquid foundation, eye liner, mascara, eye shadow, and any other milky or creamy products.

EXAMPLES

Hereinafter, the invention is more specifically described with reference to examples, which however are not intended to limit the invention. All material content percentages are by mass unless otherwise specified.

First, a description is given of the evaluation methods used for the invention.

[Stability Test]

Samples were allowed to stand at 50° C. for one month, and then their appearances were visually observed and evaluated according to the criteria below.

(Evaluation Criteria)

○: Separation was not observed at all.

Δ: Separation was hardly observed.

X: Separation in Liquid-phase (oil-phase or aqueous-phase) occurred.

[Texture (Spreadability on Skin)]

A panel of female experts (ten experts) carried out an actual use test to evaluate speadability on skin and made evaluations according to the criteria below.

(Evaluation Criteria)

⊙: All ten experts determined that spreading was light and smooth.

○: Seven to nine experts determined that spreading was light and smooth.

Δ: Three to six experts determined that spreading was light and smooth.

X: Zero to two experts determined that spreading was light and smooth.

[Texture (Stickiness)]

A panel of female experts (ten experts) carried out an actual use test to evaluate stickiness and made evaluations according to the criteria below.

(Evaluation Criteria)

⊙: All ten experts determined that there was a moist feeing with no stickiness.

○: Seven to nine experts determined that there was a moist feeing with no stickiness.

Δ: Three to six experts determined that there was a moist feeing with no stickiness.

X: Zero to two experts determined that there was a moist feeing with no stickiness.

[Texture (Lightness)]

A panel of female experts (ten experts) carried out an actual use test to evaluate lightness and made evaluations according to the criteria below.

(Evaluation Criteria)

⊙: All ten experts determined that there was lightness.

○: Seven to nine experts determined that there was lightness.

Δ: Three to six experts determined that there was lightness.

X: Zero to two experts determined that there was lightness.

[Skin Improving Effect (Skin Resilience)]

A panel of female experts (ten experts) carried out an actual use test to evaluate skin resilience and made evaluations according to the criteria below.

(Evaluation Criteria)

⊙: All ten experts determined that the skin became resilient.

○: Seven to nine experts determined that the skin became resilient.

Δ: Three to six experts determined that the skin became resilient.

X: Zero to two experts determined that the skin became resilient.

[Skin Improving Effect (Making Skin Moisturized)]

A panel of female experts (ten experts) carried out an actual use test to evaluate the effect of moisturizing the skin and made evaluations according to the criteria below.

(Evaluation Criteria)

⊙: All ten experts determined that the skin was made moisturized.

○: Seven to nine experts determined that the skin was made moisturized.

Δ: Three to six experts determined that the skin was made moisturized.

X: Zero to two experts determined that the skin was made moisturized.

Examples 1 to 7 and Comparative Examples 1 to 6

According to the formulas shown in Tables 1 and 2 below, oil-in-water type emulsion skin cosmetic creams were prepared by a conventional method. The resulting compositions (samples) were evaluated for stability, texture, and skin improving effect according to the methods and criteria described above.

In Tables 1 and 2, "vinylpyrrolidone/sodium 2-acrylamido-methylpropanesulfonate copolymer" used as the "ingredient (B)" was "ARISTOFLEX AVC" (manufactured by CLARIANT).

TABLE 1

| Ingredients | | Example 1 | 2 | 3 | 4 | 5 | 6 | 7 |
|---|---|---|---|---|---|---|---|---|
| (1) Ion-exchanged water | | Balance | Balance | Balance | Balance | Balance | Balance | Balance |
| (2) D-alanine [ingredient (A)] | | 0.1 | 3.0 | 5.0 | 0.1 | 3.0 | 3.0 | 3.0 |
| (3) Glycerin [ingredient (D)] | | 5.0 | 10.0 | 15.0 | 10.0 | 5.0 | 10.0 | 10.0 |
| (4) 1,3-butylene glycol | | 3.0 | 3.0 | 3.0 | 3.0 | 3.0 | 3.0 | 3.0 |
| (5) Vinylpyrrolidone/sodium 2-acrylamido-methylpropanesulfonate copolymer [ingredient (B)] | | 0.1 | 1.0 | 2.0 | 1.0 | 1.0 | 0.1 | 1.0 |
| (5') Carboxyvinyl polymer | | — | — | — | — | — | — | — |
| (6) Self-emulsifying glyceryl monostearate | | 3.0 | 3.0 | 3.0 | 3.0 | 3.0 | 3.0 | 3.0 |
| (7) PEG-100 stearate | | 2.0 | 2.0 | 2.0 | 2.0 | 2.0 | 2.0 | 2.0 |
| (8) Stearic acid | | 0.1 | 0.1 | 0.1 | 0.1 | 0.1 | 0.1 | 0.1 |
| (9) Palmitic acid | | 0.3 | 0.3 | 0.3 | 0.3 | 0.3 | 0.3 | 0.3 |
| (10) Sodium hydroxide | | Proper amount | Proper amount | Proper amount | Proper amount | Proper amount | Proper amount | Proper amount |
| (11) Myristyl myristate | | 2.0 | 2.0 | 2.0 | 2.0 | 2.0 | 2.0 | 2.0 |
| (12) Isodecyl neopentanoate [ingredient (C)] | | 1.0 | 8.0 | 15.0 | 8.0 | 10.0 | 1.0 | 1.0 |
| (13) Squalane | | — | — | — | — | — | — | — |
| (14) Dimethylsilicone (5 mPa·s) | | 5.0 | 5.0 | 5.0 | 5.0 | 5.0 | 5.0 | 5.0 |
| (15) Hydrogenated polyisobutene | | 5.0 | 5.0 | 5.0 | 5.0 | 5.0 | 5.0 | 5.0 |
| (16) 2-ethylhexyl-2-cyano-3,3-diphenylacrylate | | 1.0 | 1.0 | 1.0 | 1.0 | 1.0 | 1.0 | 1.0 |
| (17) Edetate | | 0.1 | 0.1 | 0.1 | 0.1 | 0.1 | 0.1 | 0.1 |
| (18) Phenoxyethanol | | 0.5 | 0.5 | 0.5 | 0.5 | 0.5 | 0.5 | 0.5 |
| (19) Perfume | | 0.1 | 0.1 | 0.1 | 0.1 | 0.1 | 0.1 | 0.1 |
| Stability | | ⊙ | ⊙ | ⊙ | ⊙ | ⊙ | ⊙ | ⊙ |
| Texture | (Spreadability on skin) | ⊙ | ⊙ | ⊙ | ⊙ | ⊙ | ⊙ | ⊙ |
| | (stickiness) | ⊙ | ⊙ | ⊙ | ⊙ | ⊙ | ⊙ | ⊙ |
| | (lightness) | ⊙ | ⊙ | ⊙ | ⊙ | ⊙ | ⊙ | ⊙ |
| Skin improving effect | (skin resilience) | ⊙ | ⊙ | ⊙ | ⊙ | ⊙ | ⊙ | ⊙ |
| | (skin moisturizing) | ⊙ | ⊙ | ⊙ | ⊙ | ⊙ | ⊙ | ⊙ |

TABLE 2

| Ingredients | | Example 1 | 2 | 3 | 4 | 5 | 6 |
|---|---|---|---|---|---|---|---|
| (1) Ion-exchanged water | | Balance | Balance | Balance | Balance | Balance | Balance |
| (2) D-alanine [ingredient (A)] | | — | 3.0 | 3.0 | 1.0 | 3.0 | 3.0 |
| (3) Glycerin [ingredient (D)] | | 5.0 | 5.0 | 5.0 | 5.0 | 5.0 | — |
| (4) 1,3-butylene glycol | | 3.0 | 3.0 | 3.0 | 3.0 | 3.0 | 3.0 |
| (5) Vinylpyrrolidone/sodium 2-acrylamido-methylpropanesulfonate copolymer [ingredient (B)] | | 1.0 | — | 1.0 | — | 1.0 | 1.0 |
| (5') Carboxyvinyl polymer | | — | — | — | 0.2 | — | — |
| (6) Self-emulsifying glyceryl monostearate | | 3.0 | 3.0 | 3.0 | 3.0 | 3.0 | 3.0 |
| (7) PEG-100 stearate | | 2.0 | 2.0 | 2.0 | 2.0 | 2.0 | 2.0 |
| (8) Stearic acid | | 0.1 | 0.1 | 0.1 | 0.1 | 0.1 | 0.1 |
| (9) Palmitic acid | | 0.3 | 0.3 | 0.3 | 0.3 | 0.3 | 0.3 |
| (10) Sodium hydroxide | | Proper amount | Proper amount | Proper amount | Proper amount | Proper amount | Proper amount |
| (11) Myristyl myristate | | 2.0 | 2.0 | 2.0 | 2.0 | 2.0 | 2.0 |
| (12) Isodecyl neopentanoate [ingredient (C)] | | 8.0 | 8.0 | — | 8.0 | — | 8.0 |
| (13) Squalane | | — | — | — | — | 8.0 | — |
| (14) Dimethylsilicone (5 mPa·s) | | 5.0 | 5.0 | 5.0 | 5.0 | 5.0 | 5.0 |
| (15) Hydrogenated polyisobutene | | 5.0 | 5.0 | 5.0 | 5.0 | 5.0 | 5.0 |
| (16) 2-ethylhexyl-2-cyano-3,3-diphenylacrylate | | 1.0 | 1.0 | 1.0 | 1.0 | 1.0 | 1.0 |
| (17) Edetate | | 0.1 | 0.1 | 0.1 | 0.1 | 0.1 | 0.1 |
| (18) Phenoxyethanol | | 0.5 | 0.5 | 0.5 | 0.5 | 0.5 | 0.5 |
| (19) Perfume | | 0.1 | 0.1 | 0.1 | 0.1 | 0.1 | 0.1 |
| Stability | | ⊙ | X | ⊙ | ○ | ⊙ | ⊙ |
| Texture | (Spreadability on skin) | ⊙ | ⊙ | Δ | ⊙ | X | Δ |
| | (stickiness) | Δ | ⊙ | X | Δ | X | ⊙ |
| | (lightness) | ⊙ | ⊙ | X | Δ | X | ⊙ |
| Skin improving effect | (skin resilience) | ⊙ | X | ⊙ | Δ | ○ | X |
| | (skin moisturizing) | Δ | ⊙ | ⊙ | Δ | ⊙ | X |

Tables 1 and 2 show that Examples 1 to 7 according to the invention are excellent in stability, texture, and skin improving effect. In contrast, not all of stability, texture, and skin improving effect are satisfactory with respect to Comparative Examples 1 to 6, which do not satisfy the requirements of the invention.

Specifically, Comparative Examples 1 to 3 and 6 lack any of the ingredients (A), (B), (C), and (D). Comparative Example 1 not containing the ingredient (A) is sticky and lacks a skin moisturizing effect. Comparative Example 2 not containing the ingredient (B) particularly has a problem with stability. Comparative Example 3 not containing the ingredient (C) is significantly inferior in texture such as spreadability on skin, stickiness, or lightness. Comparative Example 6 not containing the ingredient (D) does not produce a skin improving effect such as a skin moisturizing effect.

Comparative Example 4 containing another thickener (carboxyvinyl polymer) instead of the ingredient (B) is insufficient in texture with respect to stickiness, lightness, etc. and insufficient in skin improving effect. Comparative Example 5 containing squalane with an IOB of 0 instead of the ingredient (C) is sticky and lacks spreadability on skin and lightness, although it makes the skin resilient and moisturized.

Hereinafter, other examples of the invention are shown.

Example 8

Anti-Aging Cream

| (Ingredients) | | % by mass |
|---|---|---|
| (1) | Liquid paraffin | 2.0 |
| (2) | Decamethylcyclopentanesiloxane | 5.0 |
| (3) | Isodecyl benzoate (IOB = 23) [ingredient (C)] | 5.0 |
| (4) | Polyoxyethylene (21) stearyl ether | 2.0 |
| (5) | Polyoxyethylene (2) stearyl ether | 0.5 |
| (6) | Cetyl alcohol | 2.5 |
| (7) | Batyl alcohol | 2.0 |
| (8) | Perfume | 0.1 |
| (9) | Ion-exchanged water | q.s. |
| (10) | Dipropylene glycol | 3.0 |
| (11) | Glycerin [ingredient (D)] | 11.0 |
| (12) | Paraben | 0.15 |
| (13) | Ethanol | 3.0 |
| (14) | Potassium hydroxide | 0.4 |
| (15) | Dimethylacrylamide/sodium 2-acrylamido-2-methylpropanesulfonate crosspolymer [ingredient (B)] (Trade name: SU-POLYMER G-1, manufactured by TOHO Chemical Industry Co., Ltd.) | 0.8 |
| (16) | Citric acid | 0.01 |
| (17) | Sodium citrate | 0.09 |
| (18) | D-hydroxyproline [ingredient (A)] | 2.0 |

<Preparation Process>

Ingredients (1) to (8) were uniformly mixed and dissolved at 70° C. (oil phase). On the other hand, ingredients (9) to (18) were uniformly mixed and dissolved at 70° C. (aqueous phase). While the oil phase was gradually added to the aqueous phase kept at 70° C., the mixture was emulsified with a homomixer. After the emulsification was completed, the emulsion was rapidly cooled to 40° C. or less to give the desired anti-aging cream.

<Product Properties>

The resulting cream was evaluated in the same manner as described above for Examples 1 to 7. As a result, the cream had good texture (the evaluation was ⊙ with respect to all of skin spreadability, stickiness, and lightness), a moisturizing effect, light spreadability, and a moist feeling with lightness when applied to the skin, and also had good stability (the stability was evaluated "◯").

Example 9

O/W Emulsion-Type Sunscreen

| (Ingredients) | | % by mass |
|---|---|---|
| (1) | Octyl p-methoxycinnamate | 6.0 |
| (2) | Glyceryloctyl di-p-methoxycinnamate | 2.0 |
| (3) | 4-tert-butyl-4'-methoxybenzoylmethane | 2.0 |
| (4) | Pentaerythritol tetra (octanoate/p-methoxycinnamate) | 3.0 |
| (5) | Tripropylene glycol dineopentanoate (IOB = 0.52) [ingredient (C)] | 5.0 |
| (6) | Dimethylpolysiloxane (20 mPa·s) | 3.0 |
| (7) | Petrolatum | 0.5 |
| (8) | PEG (40) glyceryl isostearate | 1.2 |
| (9) | Sorbitan tristearate | 0.25 |
| (10) | Ion-exchanged water | balance |
| (11) | 1,3-butylene glycol | 3.0 |
| (12) | Glycerin [ingredient(D)] | 5.0 |
| (13) | Ethanol | 3.0 |
| (14) | Acrylamide/sodium 2-acrylamido-2-methylpropanesulfonate (40% in active content) [ingredient (B)] (Trade name: SEPIGEL 305, manufactured by SEPIC) | 1.0 (0.4) |
| (15) | Perfume | 0.1 |
| (16) | D-methionine [ingredient(A)] | 0.5 |

<Preparation Process>

Ingredients (1) to (9) were uniformly mixed and dissolved at 70° C. (oil phase). On the other hand, ingredients (10) to (16) were uniformly mixed and dissolved at 70° C. (aqueous phase). While the oil phase was gradually added to the aqueous phase kept at 70° C., the mixture was emulsified with a homomixer. After the emulsification was completed, the emulsion was rapidly cooled to 40° C. or less to give the desired O/W emulsion type sunscreen.

<Product Properties>

The resulting sunscreen was evaluated in the same manner as Examples 1 to 7. As a result, the sunscreen had good texture (the evaluation was ⊙ with respect to all of skin spreadability, stickiness, and lightness), a moisturizing effect, light spreadability, and a moist feeling with lightness when applied to the skin, and also had good stability (the stability was evaluated "◯").

Example 10

Whitening Cream

| (Ingredients) | | % by mass |
|---|---|---|
| (1) | Hydrogenated polyisobutene | 2.0 |
| (2) | Isododecane | 6.0 |
| (3) | Isodecyl benzoate (IOB = 0.23) [ingredient (C)] | 3.0 |
| (4) | Polyoxyethylene (30) behenyl ether | 3.0 |
| (5) | Cetyl alcohol | 2.5 |
| (6) | Batyl alcohol | 2.5 |
| (7) | Perfume | 0.1 |
| (8) | Ion-exchanged water | balance |
| (9) | 1,3-butylene glycol | 3.0 |
| (10) | Glycerin [ingredient (D)] | 6.0 |
| (11) | Arbutin | 5.0 |

-continued

| (Ingredients) | | % by mass |
|---|---|---|
| (12) | Magnesium ascorbate phosphate | 1.0 |
| (13) | Paraben | 0.15 |
| (14) | Ethanol | 3.0 |
| (15) | Potassium hydroxide | q.s. |
| (16) | (Hydroxyethyl acrylate/sodium 2-acrylamido-2-methylpropanesulfonate) copolymer (37.5% in active content) [ingredient (B)] (trade name: SIMULGEL NS, manufactured by SEPIC) | 1.3 (0.49) |
| (17) | Citric acid | 0.01 |
| (18) | Sodium citrate | 0.09 |
| (19) | D-serine [ingredient (A)] | 2.5 |

<Preparation Process>

Ingredients (1) to (7) were uniformly mixed and dissolved at 70° C. (oil phase). On the other hand, ingredients (8) to (19) were uniformly mixed and dissolved at 70° C. (aqueous phase). While the oil phase was gradually added to the aqueous phase kept at 70° C., the mixture was emulsified with a homomixer. After the emulsification was completed, the emulsion was rapidly cooled to 40° C. or less to give the desired whitening cream.

<Product Properties>

The resulting whitening cream was evaluated in the same manner as Examples 1 to 7. As a result, the cream had good texture (the evaluation was ⊙ with respect to all of skin spreadability, stickiness, and lightness), a moisturizing effect, light spreadability, and a moist feeling with lightness when applied to the skin, and also had good stability (the stability was evaluated "○").

Example 11

Whitening Cream

| (Ingredients) | | % by mass |
|---|---|---|
| (1) | Liquid paraffin | 2.0 |
| (2) | Dimethysilicone(1.5 mPa · s) | 6.0 |
| (3) | Isononyl isononanoate (IOB = 0.2) [ingredient (C)] | 3.0 |
| (4) | Polyoxyethylene (20) sorbitan monostearate | 3.0 |
| (5) | Sorbitan trioleate | 0.3 |
| (6) | Cetyl alcohol | 2.5 |
| (7) | Batyl alcohol | 1.0 |
| (8) | Perfume | 0.1 |
| (9) | 1,3-butylene glycol | 5.0 |
| (10) | Glycerin [ingredient (D)] | 7.0 |
| (11) | Ion-exchanged water | balance |
| (12) | Trimethylglycine | 0.1 |
| (13) | Potassium 4-methoxysalicylate | 2.0 |
| (14) | Phenoxyethanol | 0.2 |
| (15) | Sodium hydroxide | q.s. |
| (16) | (Hydroxyethyl acrylate/sodium 2-acrylamido-2-methylpropanesulfonate) copolymer [ingredient (B)] (trade name: SEPINOV EMT 10, manufactured by SEPIC) | 1.5 |
| (17) | Citric acid | 0.02 |
| (18) | Sodium citrate | 0.08 |
| (19) | D-glutamic acid [ingredient (A)] | 0.5 |
| (20) | D-aspartic acid [ingredient (A)] | 1.0 |

<Preparation Process>

Ingredients (1) to (8) were uniformly mixed and dissolved at 70° C. (oil phase). On the other hand, ingredients (9) to (20) were uniformly mixed and dissolved at 70° C. (aqueous phase). While the oil phase was gradually added to the aqueous phase kept at 70° C., the mixture was emulsified with a homomixer. After the emulsification was completed, the emulsion was rapidly cooled to 40° C. or less to give the desired whitening cream.

<Product Properties>

The resulting whitening cream was evaluated in the same manner as Examples 1 to 7. As a result, the cream had good texture (the evaluation was ⊙ with respect to all of skin spreadability, stickiness, and lightness), a moisturizing effect, light spreadability, and a moist feeling with lightness when applied to the skin, and also had good stability (the stability was evaluated "○").

The invention claimed is:

1. An oil-in-water type emulsion skin cosmetic composition, comprising:
   (A) a D-amino acid selected from the group consisting of D-glutamic acid, D-alanine, D-methionine, D-hydroxyproline, D-aspartic acid, D-cysteine, D-serine, and D-proline; or a salt thereof;
   (B) a homopolymer, a copolymer, or a crosspolymer comprising, as a constituent unit, 2-acrylamido-2-methylpropanesulfonic acid or cosmetically acceptable salts thereof;
   (C) an ester oil with an inorganic organic balance (IOB) value of 0.2 to 0.6; and
   (D) glycerin;
wherein the composition contains
   0.1 to 5.0% by mass of the ingredient (A),
   0.1 to 2.0% by mass of the ingredient (B),
   1.0 to 15.0% by mass of the ingredient (C), and
   5.0 to 15.0% by mass of the ingredient (D)
based on the total amount of the cosmetic composition.

2. The oil-in-water emulsion skin cosmetic composition according to claim 1, wherein the ingredient (B) is one or more selected from the group consisting of:
   a vinylpyrrolidone/2-acrylamido-2-methylpropanesulfonic acid copolymer,
   a dimethylacrylamide/2-acrylamido-2-methylpropanesulfonic acid copolymer,
   an acrylamide/2-acrylamido-2-methylpropanesulfonic acid copolymer,
   a methylenebisacrylamide-crosslinked dimethylacrylamide/2-acrylamido-2-methylpropanesulfonic acid crosspolymer,
   a hydroxyethyl acrylate/2-acrylamido-2-methylpropanesulfonic acid copolymer,
   an acrylamide/acrylic acid/2-acrylamido-2-methylpropanesulfonic acid copolymer,
   a sodium acrylate/2-acrylamido-2-methylpropanesulfonic acid copolymer,
   a homopolymer of 2-acrylamido-2-methylpropanesulfonic acid,
   a vinylformamide/2-acrylamido-2-methylpropanesulfonic acid copolymer;
and cosmetically acceptable salts thereof.

3. The oil-in-water emulsion skin cosmetic composition according to claim 1, wherein: the ingredient (C) is one or more selected from tripropylene glycol dineopentanoate (IOB=0.52), isodecyl benzoate (IOB=0.23), propylene glycol dicaprylate (IOB=0.32), isononyl isononanoate (IOB=0.2), cetyl 2-ethylhexanoate (IOB=0.52), glyceryl tri-2-ethylhexanoate (IOB=0.36), isodecyl neopentanoate (IOB=0.22), 2-ethylhexyl 2-ethylhexanoate (IOB=0.2), pentaerythritol tetra-2-ethylhexanoate (IOB=0.35), di-2-ethylhexyl succinate (IOB=0.32), and 2-ethylhexyl isononanoate (IOB=0.2).

4. The oil-in-water emulsion skin cosmetic composition according to claim 2, wherein: the ingredient (C) is one or more selected from tripropylene glycol dineopentanoate (IOB=0.52), isodecyl benzoate (IOB=0.23), propylene glycol dicaprylate (IOB=0.32), isononyl isononanoate (IOB=0.2), cetyl 2-ethylhexanoate (IOB=0.52), glyceryl tri-2-ethylhexanoate (IOB=0.36), isodecyl neopentanoate (IOB=0.22), 2-ethylhexyl 2-ethylhexanoate (IOB=0.2), pentaerythritol tetra-2-ethylhexanoate (IOB=0.35), di-2-ethylhexyl succinate (IOB=0.32), and 2-ethylhexyl isononanoate (IOB=0.2).

* * * * *